US008383251B2

(12) United States Patent
Herron et al.

(10) Patent No.: US 8,383,251 B2
(45) Date of Patent: Feb. 26, 2013

(54) SUBSTITUTED PYRENES AND ASSOCIATED PRODUCTION METHODS FOR LUMINESCENT APPLICATIONS

(75) Inventors: Norman Herron, Newark, DE (US); Mark A. Guidry, Wilmington, DE (US); Vsevolod Rostovtsev, Swarthmore, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/459,507

(22) Filed: Apr. 30, 2012

(65) Prior Publication Data

US 2012/0211734 A1 Aug. 23, 2012

Related U.S. Application Data

(62) Division of application No. 12/350,338, filed on Jan. 8, 2009, now Pat. No. 8,192,848.

(60) Provisional application No. 61/020,417, filed on Jan. 11, 2008.

(51) Int. Cl.
 *H01L 51/54* (2006.01)

(52) U.S. Cl. ........ 428/690; 428/917; 313/504; 313/505; 313/506; 585/11; 585/26; 585/250; 585/257

(58) Field of Classification Search .................... 585/11, 585/26, 250, 257; 428/690, 917; 313/504, 313/505, 506
See application file for complete search history.

(56) References Cited

U.S. PATENT DOCUMENTS

| | | | |
|---|---|---|---|
| 5,247,190 A | 9/1993 | Friend et al. | |
| 5,408,109 A | 4/1995 | Heeger | |
| 6,852,429 B1 | 2/2005 | Li et al. | |
| 6,875,524 B2 | 4/2005 | Hatwar et al. | |
| 7,173,131 B2 | 2/2007 | Saitoh et al. | |
| 7,358,409 B2 | 4/2008 | Saitoh et al. | |
| 7,375,250 B2 | 5/2008 | Saitoh et al. | |
| 7,402,681 B2 | 7/2008 | Ong et al. | |
| 7,491,450 B2 | 2/2009 | Okinaka et al. | |
| 7,651,788 B2 | 1/2010 | Seo et al. | |
| 7,709,104 B2 | 5/2010 | Saitoh et al. | |
| 2001/0053462 A1 | 12/2001 | Mishima | |
| 2002/0076576 A1 | 6/2002 | Li | |
| 2003/0118866 A1 | 6/2003 | Oh et al. | |
| 2004/0102577 A1 | 5/2004 | Hsu et al. | |
| 2004/0106003 A1 | 6/2004 | Chen et al. | |
| 2004/0127637 A1 | 7/2004 | Hsu et al. | |
| 2004/0189190 A1 | 9/2004 | Suzuri et al. | |
| 2005/0031898 A1 | 2/2005 | Li et al. | |
| 2005/0158577 A1 | 7/2005 | Ishibashi et al. | |
| 2005/0184287 A1 | 8/2005 | Herron et al. | |
| 2005/0205860 A1 | 9/2005 | Hsu et al. | |
| 2006/0052641 A1 | 3/2006 | Funahashi | |
| 2006/0113528 A1 | 6/2006 | Okinaka et al. | |
| 2006/0115678 A1 | 6/2006 | Saitoh et al. | |
| 2006/0121312 A1 | 6/2006 | Yamada et al. | |
| 2006/0154107 A1 | 7/2006 | Kubota et al. | |
| 2006/0159838 A1 | 7/2006 | Kowalski et al. | |
| 2006/0251925 A1 | 11/2006 | Hosokawa et al. | |
| 2006/0267488 A1 | 11/2006 | Saitoh et al. | |
| 2007/0063638 A1 | 3/2007 | Tokairin et al. | |
| 2007/0114917 A1 | 5/2007 | Funahashi | |
| 2007/0252511 A1 | 11/2007 | Funahashi | |
| 2007/0255076 A1 | 11/2007 | Ito et al. | |
| 2007/0292713 A9 | 12/2007 | Dobbs et al. | |
| 2007/0298530 A1 | 12/2007 | Feehery | |
| 2008/0191614 A1 | 8/2008 | Kim et al. | |
| 2008/0233433 A1 | 9/2008 | Igarashi et al. | |
| 2008/0286605 A1 | 11/2008 | Takeda | |
| 2009/0058279 A1 | 3/2009 | Takeda | |

FOREIGN PATENT DOCUMENTS

| | | |
|---|---|---|
| EP | 443861 A2 | 7/1995 |
| EP | 1437395 A2 | 7/2004 |
| EP | 1604974 A1 | 12/2005 |
| EP | 1737277 A1 | 12/2006 |
| EP | 2067766 A1 | 6/2009 |
| EP | 2067767 A1 | 6/2009 |
| JP | 04175395 A | 6/1992 |
| JP | 10251633 A | 9/1998 |
| JP | 2004010550 A | 1/2004 |
| JP | 2006140235 A | 6/2006 |
| JP | 2006151844 A | 6/2006 |
| JP | 2006219392 A | 8/2006 |
| JP | 2007186449 A | 7/2007 |
| JP | 2007208165 A | 8/2007 |
| KR | 1020090046731 A | 5/2009 |
| KR | 1020090086015 A | 8/2009 |
| KR | 1020090086920 A | 8/2009 |
| KR | 1020090093897 A | 9/2009 |
| WO | 2005052027 A1 | 6/2005 |
| WO | 2005115950 A1 | 12/2005 |
| WO | 2006001333 A1 | 1/2006 |
| WO | 2006057326 A1 | 6/2006 |
| WO | 2006090772 A1 | 8/2006 |
| WO | 2006137210 A1 | 12/2006 |
| WO | 2007004364 A1 | 1/2007 |
| WO | 2007021117 A1 | 2/2007 |
| WO | 2007100096 A1 | 9/2007 |
| WO | 2007105917 A1 | 9/2007 |
| WO | 2007108457 A1 | 9/2007 |
| WO | 2007108666 A1 | 9/2007 |
| WO | 2007129702 A1 | 11/2007 |
| WO | 2008149968 A1 | 12/2008 |
| WO | 2009028902 A2 | 3/2009 |
| WO | 2009055628 A1 | 4/2009 |

OTHER PUBLICATIONS

Park et al., Ab Initio Study of Substituted Pyrenes for Blue Organic Light-Emittnig Devices, Molecular Crystals and Liquid Crystals, vol. 444, pp. 177-184, 2006.*

"Color." (Definition) Web. Sep. 27, 2011, <http://hyperphysics.phy-astr.gsu/Hbase/vision/secpl>.

(Continued)

*Primary Examiner* — Jennifer Chriss
*Assistant Examiner* — Gregory Clark

(57) ABSTRACT

A substituted pyrene for electroluminescent applications and a method to produce the substituted pyrenes.

9 Claims, 1 Drawing Sheet

OTHER PUBLICATIONS

Gustafsson et al., "Flexible Light-Emitting Diodes Made from Soluble Conducting Polymers," Nature, 1992, vol. 357, pp. 477-479.

Maeda et al., "Alkynylpyrenes as Improved Pyrene-Based Biomolecular Probes with the Advantages of High Fluorescence Quantum Yields and Long Absorption/Emission Wavelengths," Chemisty—A European Journal (2006), 12(3), pp. 824-831.

March, Aromatization of Six-Membered Rings, Advanced Organic Chemistry, Wiley-Interscience (1992), 4th Ed., pp. 1162-1164.

Markus et al., Photoconductive Cell, Electronics and Nucleonics Dictionary, pp. 470-471 & 476 (McGraw-Hill 1966).

Minabe et al., "Electrophilic Substitution of Monosubstituted Pyrenes," Bulletin of the Chemical Society of Japan (1994), 67(1), pp. 172-179.

Negishi et al., Palladium-catalyzed Cross-coupling Substitution, Handbook of Organopalladium Chemistry for Organic Synthesis, John Wiley & Sons (2002), vol. 1, pp. 767-789.

Norman et al., "The Reactions of Pyrene with Free Radicals and with Sodium," Journal of the Chemical Society, 1958, pp. 175-179.

Sheldon et al., "The Mechanism of the Collision-induced Loss of Methane from the Trimethylsilyl Negative Ion," Perkin Transaction II: Organic and Bio-Organic Chemistry, Journal of the Chemical Society (1988), (7), pp. 1263-1268.

Wang, Photoconductive Materials, Kirk-Othmer Encyclopedai of Chemical Technology, Fourth Edition, 1996, vol. 18, pp. 837-860.

PCT International Search Report for International Application No. PCT/US2009/068922; Hyun Shik Oh, Authorized Officer; Oct. 20, 2010.

* cited by examiner

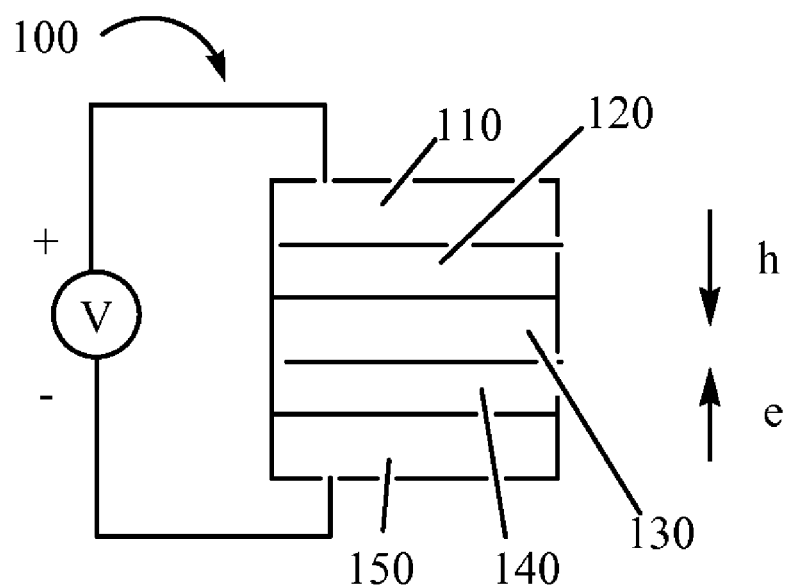

SUBSTITUTED PYRENES AND ASSOCIATED PRODUCTION METHODS FOR LUMINESCENT APPLICATIONS

RELATED APPLICATION

This application is a divisional application of and claims priority under 35 U.S.C. 120 to U.S. Ser. No. 12/350,338, filed Jan. 8, 2009 now U.S. Pat. No. 8,192,848, which in turn claimed priority under 35 U.S.C. 119 (e) from Provisional Application No. 61/020,417, filed on Jan. 11, 2008, which are incorporated by reference in their entirety.

BACKGROUND

1. Field of the Disclosure

This disclosure relates in general to the field of organic light emitting devices, and more specifically to substituted pyrene molecules utilized in these light emitting devices.

2. Description of the Related Art

Organic electronic devices capable of emitting light, such as light-emitting diodes utilized as displays for hand held devices, monitors, and television units, are present in many variations within electronic equipment. In all such devices, an organic active layer is present in conjunction with two electrical contact layers. At least one of the electrical contact layers is light-transmitting so that light can pass through the electrical contact layer. The organic active layer emits light through the light-transmitting electrical contact layer upon application of a voltage potential across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, U.S. Pat. No. 5,247,190, U.S. Pat. No. 5,408,109, and Published European Patent Application 443 861. In addition, U.S. Patent Application Publication No. US2006/0154107 discloses pyrenes for use in organic electroluminescence devices, with examples showing various (3,8)-substituted pyrene compounds. Applicants' U.S. Provisional Patent Application 60/877,985, filed Dec. 29, 2006, discloses a di-substituted pyrene dopant.

However, there is a continuing need for electroluminescent compounds, especially compounds that are blue-emitting.

SUMMARY

A hexahydro pyrene composition and aromatized pyrene resulting from oxidation of the hexahydro pyrene composition.

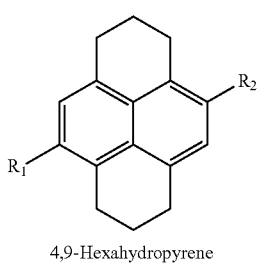

4,9-Hexahydropyrene (I)

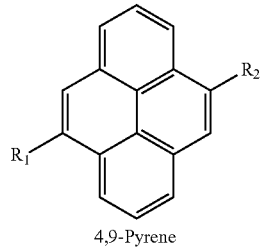

4,9-Pyrene (II)

In the above, $R_1$ and $R_2$ are independently selected from the group consisting of 2-naphthyl, 4-biphenyl, 3-biphenyl and 4-(1-naphthyl)-phenyl.

A starting material of a hexahydro pyrene compound can undergo bromination, followed by reaction to attach aryl groups and subsequent oxidation to form substituted pyrene.

There is also provided an electronic device comprising an active layer comprising at least one of the compounds described above.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

FIG. 1 is a schematic diagram of a light-emitting device (LED) of one embodiment of the present invention.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms.

DEFINITION OF TERMS

As used herein, the term "compound" is intended to mean an electrically uncharged substance made up of molecules that further consist of atoms, wherein the atoms cannot be separated by physical means. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity. The term "aryl" is intended to mean a group derived from an aromatic hydrocarbon which may be unsubstituted or substituted.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The IUPAC numbering system is used throughout, where the groups from the Periodic Table are numbered from left to right as 1-18 (CRC Handbook of Chemistry and Physics, 81st Edition, 2000).

DETAILED DESCRIPTION OF EMBODIMENTS

In one embodiment, a hexahydropyrene compound is presented, and shown below.

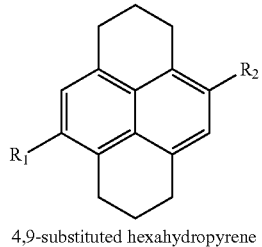

(I)

4,9-substituted hexahydropyrene

In the above, $R_1$ and $R_2$ are independently selected from the group consisting of 2-naphthyl, 4-biphenyl, 3-biphenyl and 4-(1-naphthyl)-phenyl.

Another embodiment presents a substituted pyrene shown below.

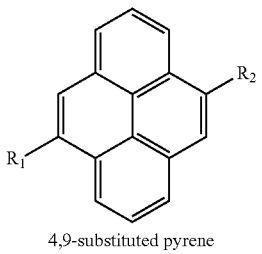

(II)

4,9-substituted pyrene

In the above, $R_1$ and $R_2$ are independently selected from the group consisting of 2-naphthyl, 4-biphenyl, 3-biphenyl and 4-(1-naphthyl)-phenyl.

The process for obtaining 4,9-substituted pyrene cores involves selective bromination of the commercially available hexahydropyrene using literature procedures. Bromination has been performed to generate the dibromo species shown in the scheme below while monobromination has also been demonstrated following a literature prep by CJ Dubois.

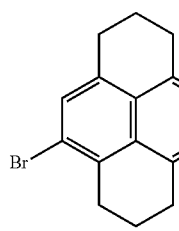

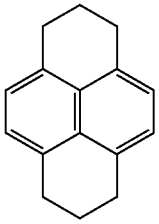

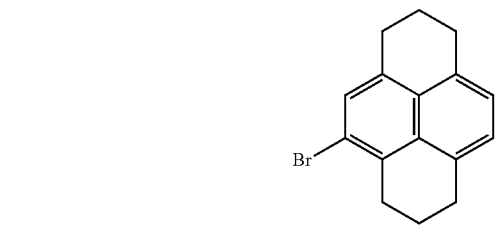

Bromination of hexahydropyrene.

A process goal has been to attempt to attach aromatic substituents to these cores using Suzuki coupling and to then aromatize the resulting hexahydro material using standard oxidation techniques with quinone oxidants.

The new pyrenes can be prepared by the Suzuki coupling of the corresponding 4,9-dibromopyrene with appropriate substituent groups using standard palladium catalysts. Typical Suzuki reactions are described by Negishi, et al., Palladium-catalyzed cross-coupling substitution. Handbook of Organopalladium Chemistry for Organic Synthesis, John Wiley & Sons (2002), [1] 767-789. Suitable reaction times are from about 5-100 hours. Suitable temperatures are from about 24-140° C. Suitable solvents include dioxanes, toluene, and tetrahydrofuran. Isolation and purification of the di-substituted pyrene product can be accomplished by techniques such as extraction, chromatography, crystallization, sublimation, used alone or in combination.

A Suzuki coupling of 4,9-dibromohexahydropyrene was conducted using 3-biphenylboronic acid. The twisted nature of the 3-biphenyl substituent often leads to improvement in solubility of derivatives. This proved to be the case and resulted in steps to separate and identify the following 3 major products in the reaction mixture:

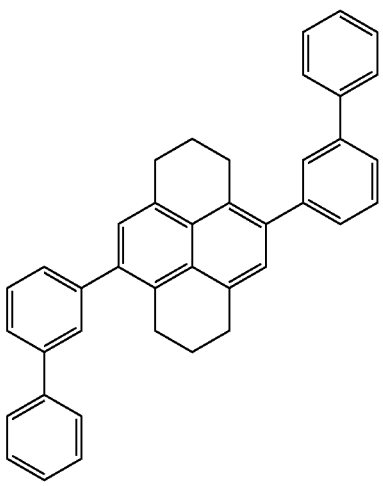

1

-continued

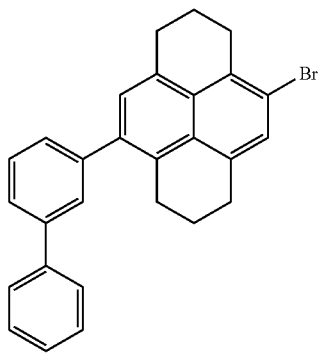
2

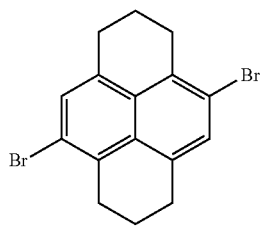
3

The desired product (1) was indeed present in low yield but the major product was the intermediate Suzuki product (2). Unreacted starting dibromide (3) completed the hexahydropyrene cored products and, overall, the indications are that the Suzuki reaction is sluggish and proceeds stepwise with a considerable build-up of the very desirable intermediate (2). Compound (2) is only one further Suzuki reaction away from an unsymmetrical hexahydropyrene core and indeed this has now been demonstrated using (2) in a Suzuki reaction with 2-naphthyl boronic acid as shown here:

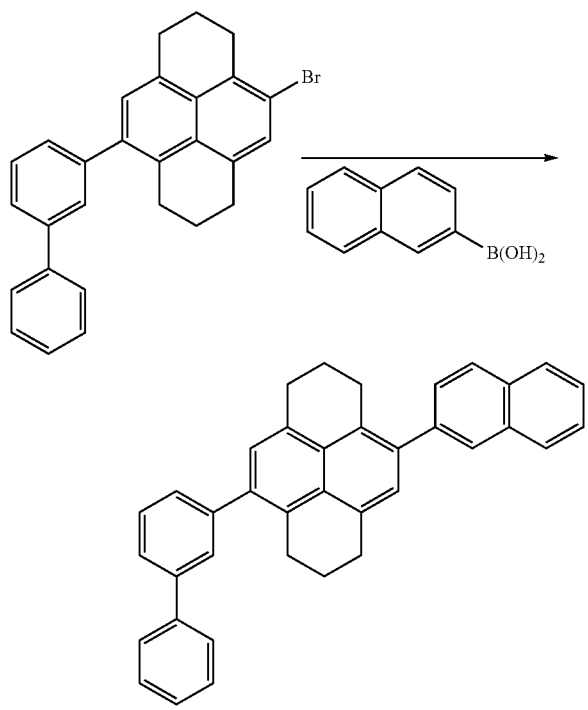

This reaction proceeded in excellent yield (>80%) to produce the desired product in good purity and with good solubility.

Aromatization of the six-membered ring is achieved by quinone agents, as described by March, Aromatization of Six-Membered Rings, Advanced Organic Chemistry, Wiley-Interscience (1992), 4$^{th}$ Ed., 1162-1164.

Electronic Device

A generic organic light emitting diode (OLED) device consists of several thin-film layers: (1) a transparent anode, usually indium tin oxide (ITO) on glass, (2) a hole transport material, (3) a luminescent material, (4) an electron transport material, and (5) a metallic cathode (e.g. Al, Al/LiF, or a low work-function metal alloy). The electrons and holes are injected from the cathode and anode into the device, and are then induced to recombine within the luminescent layer by the use of hole-transport and electron-transport layers. Recombination of electrons and holes generates an excited state of the molecular species that emits light.

A typical OLED device structure is shown in FIG. 1. The device 100 has an anode layer 110 and a cathode layer 150. Adjacent to the anode is a layer 120 comprising hole transport material. Adjacent to the cathode is a layer 140 comprising an electron transport/anti-quenching material. Between the hole transport layer and the electron transport/anti-quenching layer 130. As an option, devices frequently have a hole injection layer 115 (not shown) between the anode and the hole transport layer, and may have another electron transport layer 145 (not shown), between the cathode the first electron transport layer. Layers 115, 120, 130, 140, and 145 are individually and collectively referred to as the active layers.

Depending upon the application of the device 100, the photoactive layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary,* 470 and 476, McGraw-Hill, Inc. (1966).

Triarylmethane derivatives are particularly useful as the hole transport layer 120, and as a charge conducting host in the photoactive layer, 130. Examples of hole transport materials for layer 120 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis (naphthalen-1-yl)-N,N'-bis-(phenyl)benzidine (α-NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate.

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," *Nature vol.* 357, pp 477-479 (11 Jun. 1992). At least one of the anode and cathode is desirably at least partially transparent to allow the generated light to be observed.

Examples of materials that comprise the photoactive layer 130 include all known electroluminescent materials. These electroluminescent complexes can be used alone, or doped into charge-carrying hosts, as noted above. The di-substituted pyrenes of Formulas I and II, in addition to being useful as emissive dopants in the photoactive layer, can also act as charge carrying hosts for other emissive dopants in the photoactive layer 130.

Examples of additional electron transport materials which can be used in layer 140 include metal chelated oxinoid compounds, such as tris(8-hydroxyquinolato)aluminum ($Alq_3$); bis(2-methyl-8-quinolinolato)(para-phenyl-phenolato)aluminum(III) (BAlQ); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and 1,3,5-tri(phenyl-2-benzimidazole) benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7-diphenyl-1,10-phenanthroline (DDPA); and mixtures thereof. Layer 140 can function both to facilitate electron transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, the hole transport layer 120, the electron transport layers 140 and 160, or cathode layer 150, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like. In general, the different layers will have the following range of thicknesses: anode 110, 500-5000 Å, preferably 1000-2000 Å; hole transport layer 120, 50-2000 Å, preferably 200-1000 Å; photoactive layer 130, 10-2000 Å, preferably 100-1000 Å; electron transport layers 140 and 160, 50-2000 Å, preferably 100-1000 Å; cathode 150, 200-10000 Å, preferably 300-5000 Å. The location of the electron-hole recombination zone in the device, and thus the emission spectrum of the device, can be affected by the relative thickness of each layer. Thus the thickness of the electron-transport layer is desirably chosen so that the electron-hole recombination zone is in the light-emitting layer. The desired ratio of layer thicknesses will depend on the exact nature of the materials used.

The present disclosure also relates to an electronic device comprising at least one photoactive layer positioned between two electrical contact layers, wherein the at least one layer of the device includes the di-substituted pyrene of Formulas I or II or combination thereof. Devices frequently have additional hole transport and electron transport layers.

The pyrene compounds described herein are particularly useful as the photoactive material in layer 130, or as electron transport material in layer 140. Preferably the pyrene compounds are used as the light-emitting material in diodes. Additional materials can be present in the emitting layer with the di-substituted pyrene. For example, a fluorescent dye can be present to alter the color of emission. A diluent can also be added and such diluent can be a charge transport material or an inert matrix. A diluent can comprise polymeric materials, small molecule or mixtures thereof. A diluent can act as a processing aid, can improve the physical or electrical properties of films containing the di-substituted pyrene. Non-limiting examples of suitable polymeric materials include poly(N-vinyl carbazole), polyfluorene, and polysilane. Non-limiting examples of suitable small molecules include 4,4'-N,N'-dicarbazole biphenyl, bis(2-methyl-8-quinolinolato) (para-phenyl-phenolato)aluminum(III) (BAlQ); and tertiary aromatic amines. When a diluent is used, the pyrene is generally present in a small amount. In one embodiment, the pyrene of Formula I or Formula II, or combination, is less than 20% by weight, based on the total weight of the layer. In another embodiment, the di-substituted pyrene of Formula I or Formula II, or combination, is less than 10% by weight, based on the total weight of the layer.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials are also important considerations in selecting the electron and hole transport materials.

It is understood that the efficiency of devices made with the di-substituted pyrenes described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A composition comprising:

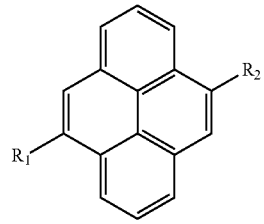

wherein $R_1$ and $R_2$ are Independently selected from the group consisting of 2-naphthyl, 4-biphenyl, 3-biphenyl and 4-(1-naphthyl)-phenyl, with the proviso that R1 and R2 are distinct from one another.

2. The composition of claim 1 wherein $R_1$ is 2-naphthyl and $R_2$ is 4-biphenyl.

3. The composition of claim 1 wherein $R_1$ is 2-naphthyl and $R_2$ is 4-(1-naphthyl)-phenyl.

4. The composition of claim 1 wherein $R_1$ is 2-naphthyl and $R_2$ is 3-biphenyl.

5. A composition comprising:

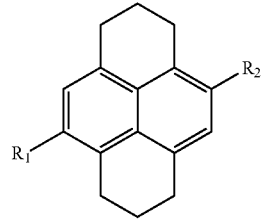

wherein $R_1$ and $R_2$ are independently selected from the group consisting of 2-naphthyl, 4-biphenyl, 3-biphenyl and 4-(1-naphthyl)-phenyl.

6. The composition of claim 1 wherein $R_1$ and $R_2$ are distinct from one another.

7. The composition of claim 6 wherein $R_1$ is 2-naphthyl and $R_2$ is 4-biphenyl.

8. The composition of claim 6 wherein $R_1$ is 2-naphthyl and $R_2$ is 4-(1-naphthyl)-phenyl.

9. The composition of claim 6 wherein $R_1$ is 2-naphthyl and $R_2$ is 3-biphenyl.

* * * * *